(12) United States Patent
Brannan

(10) Patent No.: US 12,076,223 B2
(45) Date of Patent: Sep. 3, 2024

(54) METHODS AND TOOLS FOR TREATING DISEASED TISSUE

(71) Applicant: COVIDIEN LP, Mansfield, MA (US)

(72) Inventor: Joseph D. Brannan, Lyons, CO (US)

(73) Assignee: COVIDIEN LP, Mansfield, MA (US)

(*) Notice: Subject to any disclaimer, the term of this patent is extended or adjusted under 35 U.S.C. 154(b) by 609 days.

(21) Appl. No.: 15/677,170

(22) Filed: Aug. 15, 2017

(65) Prior Publication Data

US 2019/0053886 A1 Feb. 21, 2019

(51) Int. Cl.
*A61B 18/14* (2006.01)
*A61B 10/02* (2006.01)
(Continued)

(52) U.S. Cl.
CPC ........ *A61F 2/0063* (2013.01); *A61B 10/0233* (2013.01); *A61B 17/3468* (2013.01);
(Continued)

(58) Field of Classification Search
CPC ............ A61F 2/0063; A61F 2002/0072; A61F 2210/0004; A61F 2220/0016; A61F 2250/0067; A61F 2250/0096; A61B 34/20; A61B 17/3468; A61B 18/1815; A61B 2034/2051; A61B 2090/378; A61B 10/04; A61B 10/06; A61B 2010/0216; A61B 2018/00577; A61B 2018/1838; A61B 2018/1846; A61B 2018/1853;
(Continued)

(56) References Cited

U.S. PATENT DOCUMENTS

| | | | |
|---|---|---|---|
| 6,770,070 B1 * | 8/2004 | Balbierz | ......... A61B 17/00491 606/41 |
| 9,119,650 B2 | 9/2015 | Brannan et al. | |

(Continued)

FOREIGN PATENT DOCUMENTS

| | | |
|---|---|---|
| EP | 2777591 A1 | 9/2014 |
| WO | 2016/033066 A1 | 3/2016 |

(Continued)

OTHER PUBLICATIONS

Ma, D., Dumont, T.M., Kosukegawa, H et al. High Fidelity Virtual Stenting (HiFiVS) for Intracranial Aneurysm Flow Diversion: In Vitro and In Silico . Ann Biomed Eng 41, 2143-2156 (2013). https://doi.org/10.1007/s10439-013-0808-4 (Year: 2013).*

(Continued)

*Primary Examiner* — Jaymi E Della
(74) *Attorney, Agent, or Firm* — Carter, DeLuca & Farrell LLP

(57) ABSTRACT

A kit for delivering microwave ablative energy to tissue and methods for using the kit are included. The kit includes an access catheter, an implant deployment tool, and a microwave delivery device. The implant deployment tool is configured to be inserted into the access catheter and has an implant disposed therein in a contracted state and being slidable out of a distal opening and expandable into an expanded state. The microwave delivery device is configured to deliver the microwave ablative energy to the tissue and to be advanced through the access catheter and slidably disposable within the implant when the implant is in the expanded state.

18 Claims, 18 Drawing Sheets

(51) Int. Cl.
| | |
|---|---|
| *A61B 17/34* | (2006.01) |
| *A61B 18/18* | (2006.01) |
| *A61B 34/20* | (2016.01) |
| *A61F 2/00* | (2006.01) |
| *A61M 5/00* | (2006.01) |
| *A61M 25/06* | (2006.01) |
| *A61M 31/00* | (2006.01) |
| *A61B 10/04* | (2006.01) |
| *A61B 10/06* | (2006.01) |
| *A61B 18/00* | (2006.01) |
| *A61B 90/00* | (2016.01) |
| *A61K 9/00* | (2006.01) |

(52) U.S. Cl.
CPC .......... *A61B 18/1815* (2013.01); *A61B 34/20* (2016.02); *A61M 5/002* (2013.01); *A61M 25/0662* (2013.01); *A61M 31/002* (2013.01); *A61B 2010/0216* (2013.01); *A61B 2010/0225* (2013.01); *A61B 10/04* (2013.01); *A61B 2010/045* (2013.01); *A61B 10/06* (2013.01); *A61B 2018/00023* (2013.01); *A61B 2018/00511* (2013.01); *A61B 2018/00529* (2013.01); *A61B 2018/00577* (2013.01); *A61B 2018/00982* (2013.01); *A61B 18/14* (2013.01); *A61B 18/1487* (2013.01); *A61B 2018/1838* (2013.01); *A61B 2018/1846* (2013.01); *A61B 2018/1853* (2013.01); *A61B 2018/1861* (2013.01); *A61B 2034/2051* (2016.02); *A61B 2034/2063* (2016.02); *A61B 2090/378* (2016.02); *A61F 2002/0072* (2013.01); *A61F 2210/0004* (2013.01); *A61F 2210/0019* (2013.01); *A61F 2220/0016* (2013.01); *A61F 2250/0067* (2013.01); *A61F 2250/0096* (2013.01); *A61K 9/0002* (2013.01); *A61M 2205/0238* (2013.01); *A61M 2205/0266* (2013.01); *A61M 2205/04* (2013.01); *A61M 2205/051* (2013.01)

(58) Field of Classification Search
CPC ............ A61M 25/0662; A61M 31/002; A61M 2205/0238; A61M 2205/0266; A61M 2205/04; A61M 2205/051; A61N 5/1007; A61N 2005/1011
See application file for complete search history.

(56) References Cited

U.S. PATENT DOCUMENTS

| | | | |
|---|---|---|---|
| 9,247,992 B2 | 2/2016 | Ladtkow et al. | |
| 2002/0058932 A1* | 5/2002 | Moorman | A61B 18/1477 606/41 |
| 2003/0018362 A1* | 1/2003 | Fellows | A61B 18/1492 607/5 |
| 2004/0243218 A1* | 12/2004 | Schaeffer | A61F 2/91 623/1.15 |
| 2005/0149170 A1* | 7/2005 | Tassel | A61B 5/028 623/1.15 |
| 2009/0104243 A1* | 4/2009 | Utkhede | A61F 9/0017 424/423 |
| 2009/0143759 A1 | 6/2009 | Van Dam et al. | |
| 2010/0004650 A1 | 1/2010 | Ormsby et al. | |
| 2010/0274188 A1* | 10/2010 | Chang | A61B 1/227 604/96.01 |
| 2014/0052125 A1* | 2/2014 | Bra | A61B 18/1492 606/33 |
| 2014/0180380 A1* | 6/2014 | Kelly | A61F 2/966 623/1.11 |
| 2014/0236146 A1* | 8/2014 | McLawhorn | A61B 18/1492 606/41 |
| 2014/0257272 A1* | 9/2014 | Clark, III | A61M 37/00 606/37 |
| 2015/0045784 A1 | 2/2015 | Kunis | |
| 2016/0058507 A1 | 3/2016 | Dickhans | |
| 2016/0235431 A1* | 8/2016 | Brown | A61B 17/3472 |
| 2016/0317224 A1 | 11/2016 | Girotto et al. | |
| 2016/0317225 A1 | 11/2016 | Girotto et al. | |
| 2016/0317229 A1 | 11/2016 | Girotto et al. | |
| 2016/0317230 A1 | 11/2016 | Girotto et al. | |
| 2016/0317231 A1 | 11/2016 | Girotto et al. | |
| 2016/0331567 A1 | 11/2016 | Nita | |
| 2017/0231695 A1 | 8/2017 | Dickhans | |

FOREIGN PATENT DOCUMENTS

| | | |
|---|---|---|
| WO | 2016176549 A1 | 11/2016 |
| WO | 2016179527 A1 | 11/2016 |

OTHER PUBLICATIONS

Extended European Search Report issued in corresponding Appl. No. EP 18188995.7 dated Jan. 14, 2019 (10 pages).

European Examination Report issued in corresponding Appl. No. EP 18 188 995.7 dated Feb. 8, 2021 (7 pages).

* cited by examiner

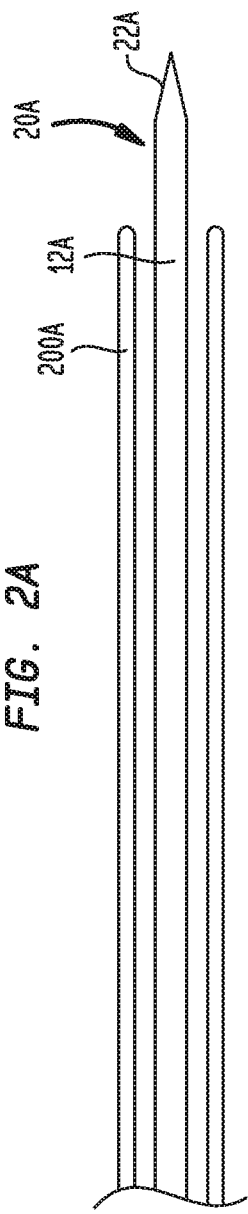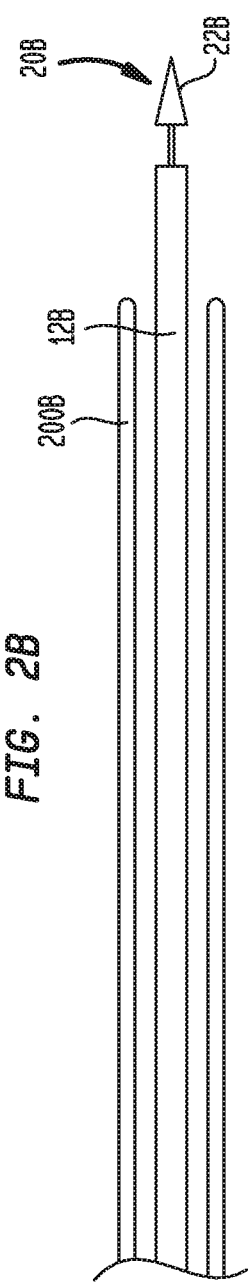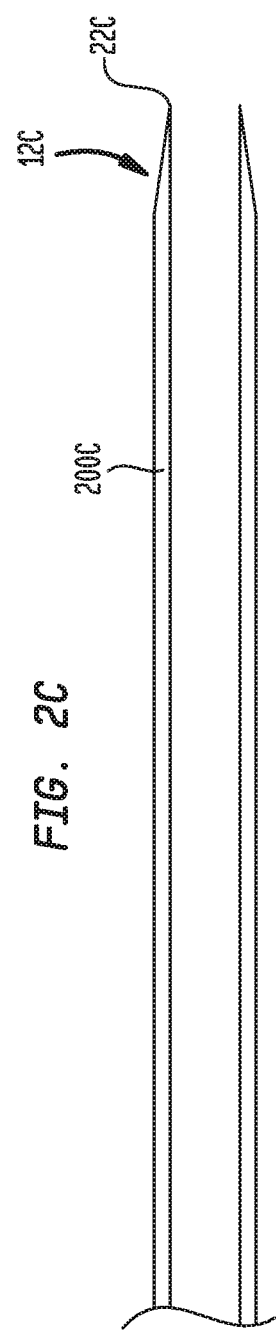

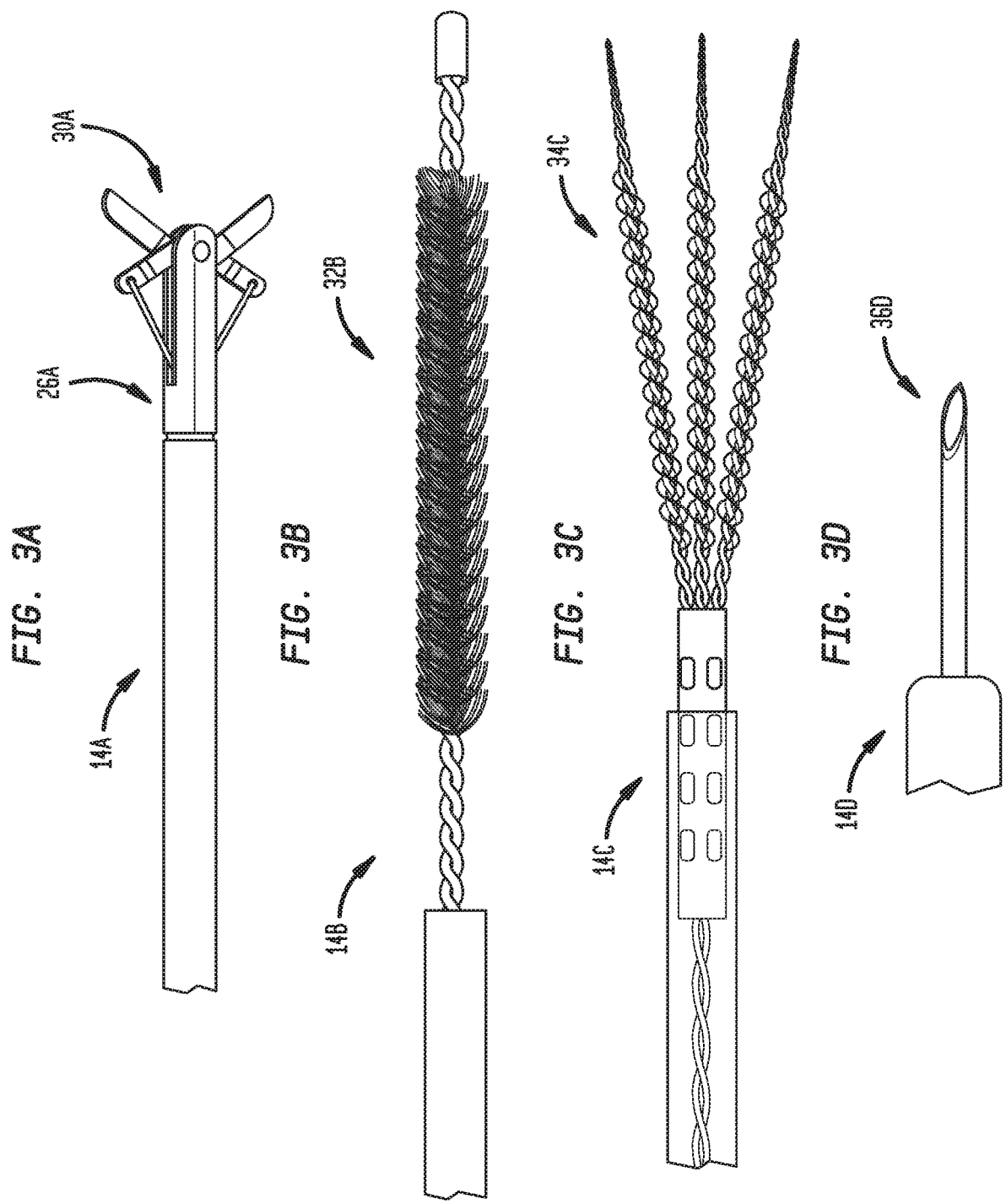

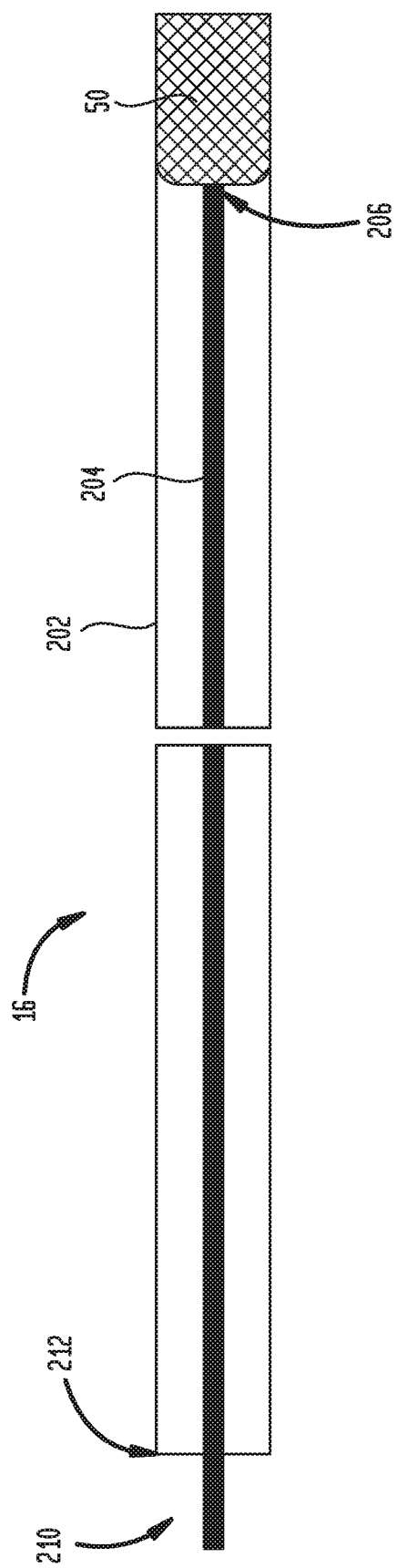

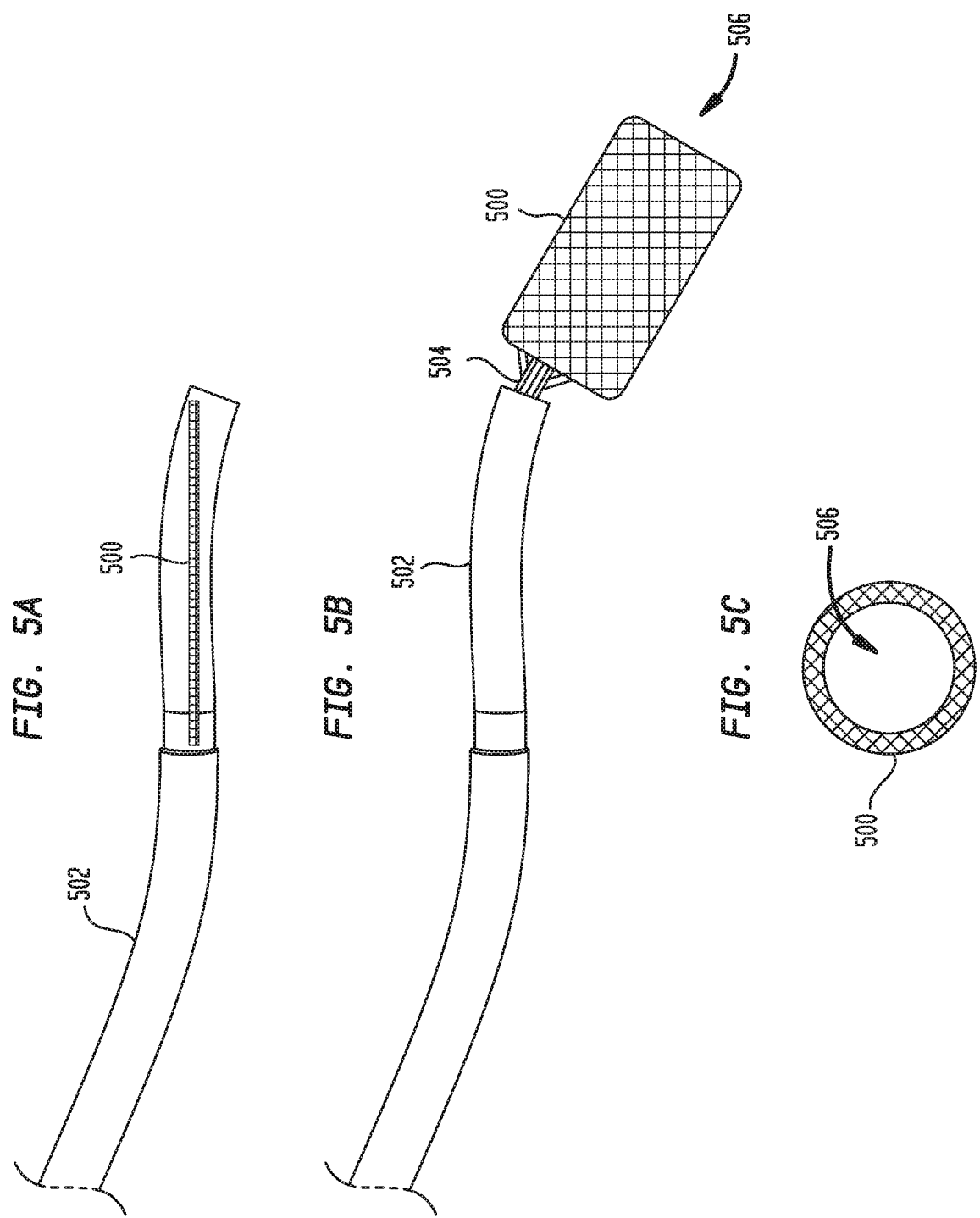

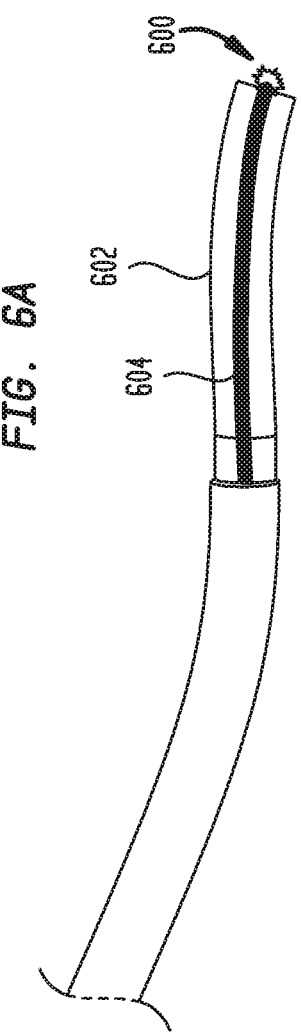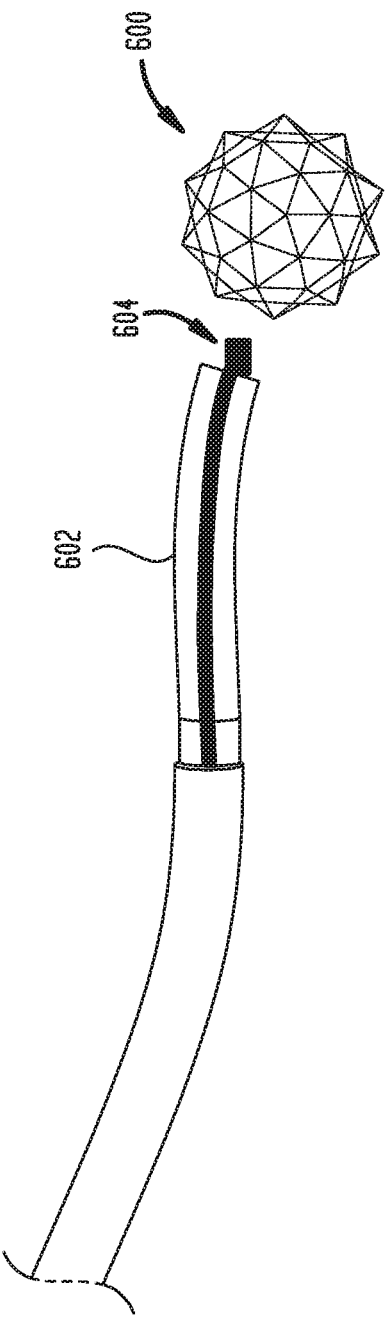

METHODS AND TOOLS FOR TREATING DISEASED TISSUE

BACKGROUND

1. Technical Field

The present disclosure relates to microwave surgical devices and tools for use with the surgical devices in tissue ablation applications.

2. Discussion of Related Art

Treatment of certain diseases requires the destruction of malignant tissue growths, e.g., tumors. In this regard, electrosurgical devices utilizing electromagnetic radiation have been developed to heat and destroy tumor cells. For example, apparatus for use in ablation procedures include a power generation source, e.g., a microwave or radio frequency (RF) electrosurgical generator that functions as an energy source, and a surgical instrument (e.g., ablation probe having an antenna assembly) for directing energy to the target tissue. The generator and surgical instrument are typically operatively coupled by a cable assembly having a plurality of conductors for transmitting energy from the generator to the instrument, and for communicating control, feedback and identification signals between the instrument and the generator.

During treatment, the ablation probe may be inserted into tissues where cancerous tumors have been identified. Once the probe is positioned, electrosurgical energy is passed through the probe and into surrounding tissue to form an "ablation zone." The energy applied to the tissue denatures the cancerous cells at elevated temperatures that are slightly lower than temperatures normally injurious to healthy cells.

Although the application of ablative energy is useful for destroying cancerous cells, improved control of the ablative energy is desired. Specifically, by controlling the ablative energy with more precision, the surgeon may be permitted to perform the ablative procedure with more specificity and accuracy. As a result, cancer cells may be more discriminately destroyed over normal cells.

SUMMARY

According to an aspect of the present disclosure, a kit for treating disease tissue is provided. The kit includes an access catheter, an implant deployment tool, and a microwave delivery device. The implant deployment tool is configured to be inserted into the access catheter and has an implant disposed therein in a contracted state and being slidable out of a distal opening and expandable into an expanded state. The microwave delivery device is configured to deliver the microwave ablative energy to the tissue and to be advanced through the access catheter and slidably disposable within the implant when the implant is in the expanded state.

In another aspect of the present disclosure, the implant is doped with radioactive material.

In another aspect of the present disclosure, the implant includes a drug.

In another aspect of the present disclosure, the implant includes a biologic, including an immune regulant such as a suppressant or accentuate.

In still another aspect of the present disclosure, the implant includes a shape memory material formed as a plurality of tines, wherein one or more of the tines folds over itself in the contracted state, and the plurality of tines form a basket in the expanded state.

In another aspect of the present disclosure, the implant comprises a plurality of tines, and a first tine of the plurality of tines has an end portion that, upon deployment out of a distal opening of the implant deployment tool, extends radially relative to a longitudinal axis of the deployment tool. In another embodiment, a second tine of the plurality of tines has an end portion that, upon deployment out of the distal opening of the deployment tool, extends radially relative to the longitudinal axis of the deployment tool, and an angle of deployment of the first tine is less than an angle of deployment of the second tine.

In another aspect of the present disclosure, the implant is deployed with a shape memory alloy forming a wire basket in the expanded state.

In another aspect of the present disclosure, the implant comprises a textile or other biologically absorbable material such as oxidized cellulose.

In another aspect of the present disclosure, the textile includes a hydrogel.

According to another aspect of the present disclosure, a method of treating tissue is provided. The method includes deploying an implant at a target area of tissue, positioning a radiating portion of a microwave ablation device adjacent the target area of the tissue, and generating microwave energy using a microwave generator to deliver microwave ablative energy to a radiating portion of a microwave ablation device. In various embodiments, the radiation portion may include the conductive portion of an expandable deployment device. The conductive portion may be recovered following ablation application, while the implant is left within the region of therapeutic delivery.

In an aspect of the present disclosure, the positioning includes placing the radiating portion of the microwave ablation device proximate to the implant or at a feed point prior to generating the microwave energy. In various embodiments, the feed point of the radiating portion may be positioned proximally, centrally, or distally with respect to the origin of the deployment mechanism.

In another aspect of the present disclosure, the method also includes deploying the implant after positioning the radiating portion and generating the microwave energy.

In another aspect of the present disclosure, the method also includes disposing an access catheter in the tissue, the access catheter having an opening adjacent to the target area of the tissue, advancing an implant delivery tool having the implant disposed at a distal portion thereof through the opening of the access catheter, deploying the implant at the target area of the tissue, and withdrawing the implant delivery tool.

In another aspect of the present disclosure, deploying the implant includes positioning the implant in the tissue, the implant being in a contracted state, and withdrawing the implant delivery tool from the implant to expand the implant to an expanded state.

In still another aspect of the present disclosure, deploying the implant includes positioning the implant in the tissue, the implant being in a contracted state, and advancing the implant out of a distal opening of the implant delivery tool to expand the implant to an expanded state.

In another aspect of the present disclosure, the method includes delivering a substance to the target area of the tissue, the substance being disposed on the implant. According to an aspect, the substance includes a drug. According to another aspect, the substance includes a radioactive material. In another aspect of the present disclosure, the substance includes a biologic.

Any of the above aspects and embodiments of the present disclosure may be combined without departing from the scope of the present disclosure.

BRIEF DESCRIPTION OF THE DRAWINGS

Objects and features of the presently disclosed system and method will become apparent to those of ordinary skill in the art when descriptions of various embodiments thereof are read with reference to the accompanying drawings, of which:

FIGS. 2A-2C are cross-section views of various embodiments of an access catheter including an access tool for use in treating tissue, in accordance with an embodiment of the present disclosure;

FIGS. 3A-3D are perspective view of various embodiments of biopsy tools for use in treating tissue, in accordance with an embodiment of the present disclosure;

FIG. 4 is a cross-section view of an implant delivery tool including an implant for use in treating tissue, in accordance with an embodiment of the present disclosure;

FIGS. 5A-5C are various views of an implant for use with the microwave ablation system for treating tissue, according to an embodiment of the present disclosure;

FIGS. 6A-6B are various views of an implant for use with the microwave ablation system for treating tissue, according to another embodiment of the present disclosure;

DETAILED DESCRIPTION

Figure 1:
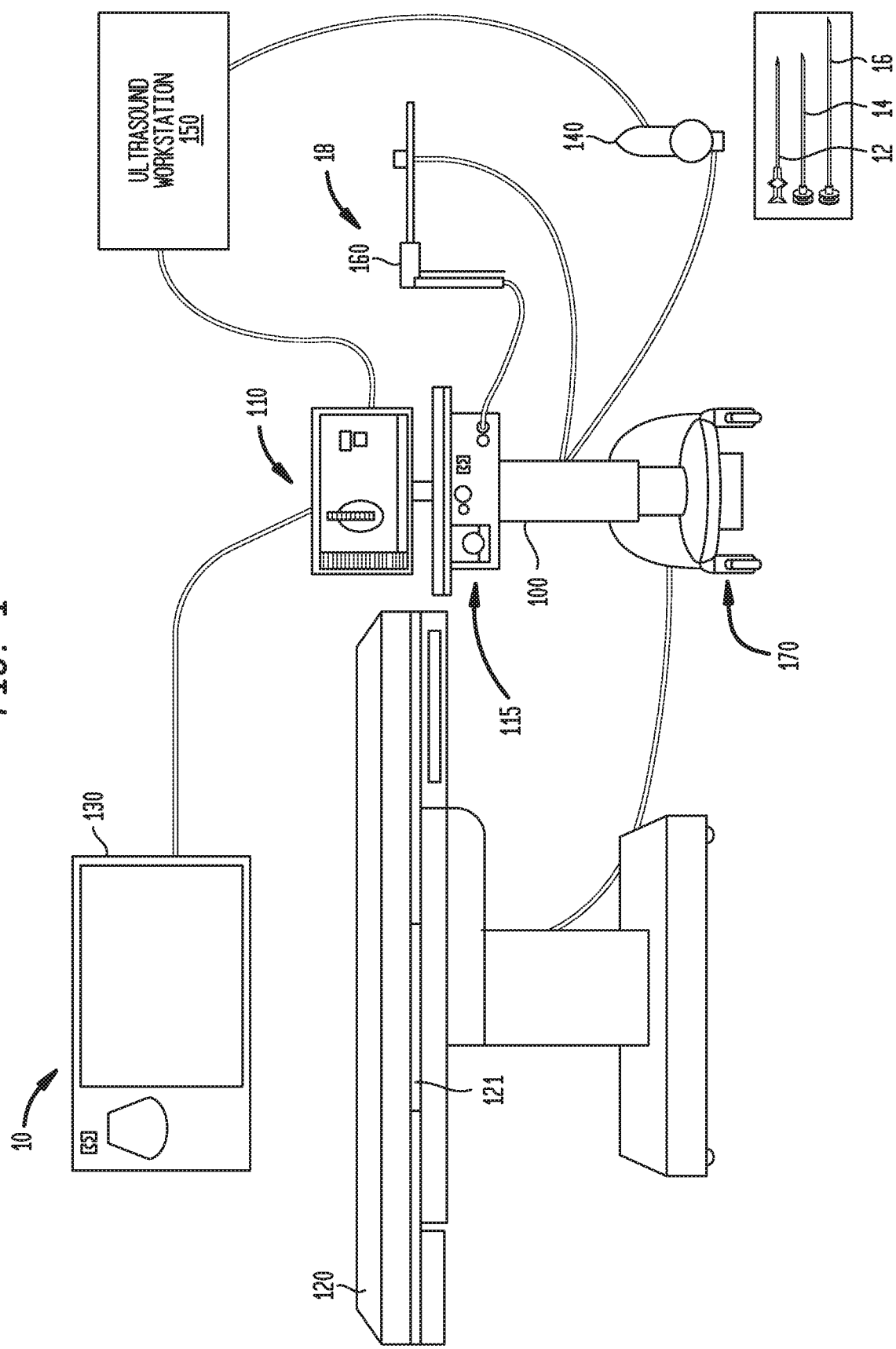
FIG. 1 is a schematic diagram of a microwave ablation system in accordance with an illustrative embodiment of the present disclosure.

The present disclosure is directed generally to tools that may be used with a microwave or radio frequency ablation device, or used with a thermo-ablation device that provides thermal or cryotherapeutic modalities. In an embodiment, the tools include an implant impregnated or doped with a drug, biologic, marker, or other substance, which may be used to deliver anti-carcinogenic drugs or radiation during treatment of tissue in a target area of a kidney, liver or other solid tissue. In another embodiment, an implant is used with a microwave ablation device to determine and control the size and shape of an ablation zone formed by ablative energy emitted from a tip of a microwave ablation device.

One or more of the tools may be provided as a kit. In an embodiment, the kit is configured for delivering microwave ablative energy to tissue includes an access catheter, an implant deployment tool, and a microwave delivery device. The implant deployment tool is configured to be inserted into the access catheter and has an implant disposed therein in a contracted state and being slidable out of a distal opening and expandable into an expanded state. The microwave delivery device is configured to deliver the microwave ablative energy to the tissue and to be advanced through the access catheter and slidably disposable within the implant when the implant is in the expanded state.

The present disclosure is also directed to methods of using the kit, tools, and/or devices to treat diseased tissue. According to an embodiment, an access catheter is inserted into a patient's airway or through an access opening, such as a percutaneous or operative access to a region of interest, to an area adjacent to a target area in the tissue to provide an access path thereto. An access tool is advanced through the access catheter, either before or after insertion of the access catheter into the patient, and is used to puncture the tissue to provide access to the target area. The access tool may be removed, in an embodiment, and a biopsy tool may be used to obtain a tissue sample from tissue in the target area, or if the access tool is incorporated into the access catheter and remains in position, the biopsy tool is advanced through the access catheter to obtain the tissue sample. In still another embodiment, the biopsy tool is incorporated into the access tool, and hence the access tool is not removed and is used to obtain the tissue sample. After obtaining the tissue sample, the biopsy or access tool may be removed, and an ablation tool advanced through the access catheter to ablate tissue in the target area, in an embodiment. In another embodiment, the access tool may incorporate an ablation tool and is used to ablate the tissue in the target area. In various embodiments, the access tool can be combined with an energy delivery device to provide tissue acquisition and energy delivery capabilities in one device. In various embodiments, the tissue sample can be loaded into a proximal cavity of the combined device prior to energy delivery. The ablation tool is then removed, and an implant delivery tool is advanced through the access catheter to the target area. The implant, which is in a contracted state and impregnated or doped with a drug, biologic, marker, or other substance, is deployed, for example, by advancing the implant delivery tool out of a distal opening of the access catheter. Once deployed, the implant is expanded to its expanded state. The implant delivery tool is then removed, while the implant remains in the tissue.

In accordance with another embodiment, after the implant is deployed into its expanded state and the implant delivery tool is removed from the access catheter. The ablation tool is advanced through the access catheter until a tip of the ablation tool is positioned proximate the implant. The tissue in the target area is ablated using the ablation tool. In another embodiment, the access tool may incorporate the ablation tool and its tip is positioned proximate the implant and used to ablate the tissue in the target area. The ablation or access tool is then removed.

Although contemplated to be implemented in the liver or kidney, the embodiments described herein are not limited to application of any particular tissue or organ for treatment, indeed, it is contemplated that the systems and methods of the present disclosure may be used to treat pancreatic tissue, gastrointestinal tissue, interstitial masses, and other portions of the body known to those of skill in the art to be treatable via microwave ablation. These and other aspects of the present disclosure are described in greater detail below.

Hereinafter, embodiments of energy-delivery devices with a probe assembly and systems including the same of the present disclosure are described with reference to the accompanying drawings. Like reference numerals may refer to similar or identical elements throughout the description of the figures. As shown in the drawings and as used in this description, and as is traditional when referring to relative positioning on an object, the term "proximal" refers to that portion of the apparatus, or component thereof, closer to the user and the term "distal" refers to that portion of the apparatus, or component thereof, farther from the user.

It will be appreciated that the procedures described herein for treating tissue may be implemented percutaneously, laparoscopically, operatively, transcutaneously, endobronchially or with the use of a catheter-type applicator, such as a working channel or sheath. According to an embodiment, various tools, including an access tool, a biopsy tool, a microwave ablation system, an implant delivery tool, and an implant may be employed to carry out the procedures. With reference to FIG. 1, an example of an exemplary system 10 is depicted including a tray, on which an access tool 12, a biopsy tool 14, and an implant delivery tool 16 may be disposed, which may be used in conjunction with a microwave ablation system 18 during an ablation procedures described in the present disclosure.

The access tool 12 may be any one of numerous types of tools configured to puncture tissue to form a path from an environment external to a patient to a target area of tissue within the patient. As depicted in FIG. 2A, the access tool 12A may be configured to operate with an access catheter 200A, in an embodiment. For example, the access tool 12A may be configured as a separate device from the access catheter 200A. In this regard, the access tool 12A has an outer diameter that is suitable to permit advancement of the access tool 12A through the access catheter 200A. In order to puncture tissue, the access tool 12A has a distal portion 20A including a piercing tip 22A. The piercing tip 22A is coupled to or formed on the distal portion 20A of the access tool 12A, in an embodiment. In various embodiments, tissue puncture can be accomplished using endovascular access tools such as chiba needles, wires, and dilators, and using procedures such as skin nicks or more invasive tissue division techniques involving scalpel or electrosurgical devices. In another embodiment, as illustrated in FIG. 2B, an access tool 12B includes a piercing tip 22B is configured to be extended or retracted through an opening formed in a distal portion 20B, and hence, is slidable relative to a remainder of the access tool 12B. In another embodiment illustrated in FIG. 2C, an access tool 12C is formed as part of the access catheter 200C and is configured to operate with an obturator (not shown). Here, the access tool 12C has an inner diameter that is suitable to permit the advancement of the biopsy tool 14 (FIG. 1), the implant delivery tool 16 (FIG. 1), and a microwave ablation device 24 (FIG. 8) of the microwave ablation system 18 (FIG. 1). Additionally, in such an embodiment, the access tool 12C has a piercing tip 22C disposed or formed as an extension of the tool 12C, also permitting the tools 14, 16, and 24 to pass through. In accordance with still another embodiment, an access tool 12 is formed as part of the microwave ablation device 24. In this regard, the access tool 12 has a piercing tip 22 disposed or formed as an extension of the microwave ablation device 24.

The biopsy tool 14 is configured to be suitable for obtaining a tissue sample from the target area of the tissue. The tissue sample (biopsy) may be obtained from pre-treated or post-treated tissue. Tumor biology markers are detectable on coagulated disease. A deployment mechanism may reside while tissue treatment occurs, and subsequent recovery of tissue residuals on the mechanism would contain sufficient material to determine tissue biology. The deployment mechanism may have geometric features, such as notches, configured to collect tissue samples from encountered tissue. In an embodiment as illustrated in FIG. 3A, a biopsy tool 14A has a distal end portion 26A coupled to a proximal manipulator (not illustrated), which when actuated and suitably manipulated, causes the distal end portion 26A to, in response to the manipulation, cut and collect tissue. In an embodiment, the distal end portion 26A may be in the form of jaws 30A forming forceps that are configured to grasp the tissue. In another embodiment, a depicted in FIG. 3B, a biopsy tool 14B is provided with a brush portion 32B for the collection of cells. In still another embodiment, as shown in FIG. 3C, a biopsy tool 14C includes a triple needle brush configuration 34B for piercing and trapping tissue on each needle. In still another embodiment, as depicted in FIG. 3D, a biopsy tool 14D may include a cutting edge 36C to obtain a core sample of tissue. In still other embodiment, not shown, the biopsy tool has a punch for punching a hole in the tissue, a blade to remove tissue (not shown) or the like. Although depicted as a standalone device, the biopsy tool 14 may be configured as part of the access tool 12.

Turning now to FIG. 4, the implant delivery tool 16 is configured to deliver an implant 50 into a target area of the tissue. In particular, the implant delivery tool 16 has a distal portion on which the implant 50 is temporarily coupled. In an embodiment, the implant delivery tool 16 is an assembly including a tube 202 and a wire 204 slidably disposed in the tube 202. The wire 204 has a proximal portion 210 that extends outside of a proximal end 212 of the tube 202 to permit the surgeon to manipulate the advancement of the wire 204 through the tool 16. A distal portion 206 of the wire 204 is maintained within the tube 202 prior to deployment of the implant 50, and the implant 50 is coupled to the distal portion 206 in a contracted state. The implant 50 can be coupled to the implant delivery tool 16 in various ways. For example, the implant 50 may be an oxidized cellulose mesh that is carried by expandable conductive tines. The mesh may be directionally biased to retain its position on the implant delivery tool 16, such that when the conductive tines pull back, the implant retains its position.

The implant 50 may have any one of numerous configurations, depending on a desired treatment for which the implant 50 will be used. For example, the implant 50 may be used as a bioabsorbable drug delivery mechanism, a short duration or long duration drug delivery mechanism, a thermally activated drug delivery mechanism, a radioactive material delivery mechanism, or another substance delivery mechanism. In this regard, the implant 50 may be made up of one or more materials, including but not limited to metals, textiles, polymers or other materials capable of being formed into a first configuration (e.g., the contracted state) and expanding into a second configuration (e.g., an expanded state). Suitable metals capable of expanding from a contracted state include, but are not limited to shape memory alloys, such as Nitinol, metals having a high spring constant such as stainless steel, and the like. Suitable delivery substrate may be made of oxidized cellulose, biologically implantable textiles, or other materials that will be known to persons skilled in the art. To deliver substances to the target tissue, the implant 50 may be doped with a drug, radioactive material, biologic or another substance, depending on a desired treatment to be performed.

With reference to FIGS. 5A-5C, a cylindrical plug 500 is employed as implant 50, in an embodiment. In the contracted state, the plug 500 may be temporarily connected to a distal portion of the wire 504 and may be disposed in the tube 502 of the implant delivery tool. Cylindrical plug 500 may have a length, when in a contracted state, that is greater than its length in the expanded state, and/or may have a diameter, when in the contracted state, that is less than its diameter when in the expanded state. The plug 500 may be formed of wire mesh or of woven wire material so that the plug 500 may remain elongated when in the contracted state. Although depicted as fully elongated in the contracted state, the plug 500 may be folded over itself one or more times, in another embodiment. To deploy the plug 500 into its expanded state, the wire 504 may be pulled, which thereby pulls a distal portion of the plug 500 toward itself to shorten its length and expands its diameter. In another embodiment, the plug 500 is formed of a shape memory alloy and deploys into the expanded state upon application of heat, either through the use of a device or by virtue of the temperature change from room temperature to body temperature. In an embodiment, when in the expanded state, the plug 500 has an open end 506 configured to receive a tip portion of microwave ablation device 24. The plug 500 may be opened on both ends or open only on one end. In an embodiment, the plug 500 is covered with a textile material is doped with a substance to be delivered to tissue. For example, the plug 500 may be lined or coated with the substance or a doped sleeve may be disposed around the plug 500.

Turning now to FIGS. 6A-6B, a spherical plug 600 is employed as the implant, in an embodiment. Here, in the contracted state, the plug 600 may be disposed on the distal portion of the wire 604 and may be in the form of a compact wire ball having a density that is greater than its density when in the expanded state and a diameter that is less than its diameter when in the expanded state. The plug 600 may be formed of a shape memory alloy woven into a configuration such that, when heated, deploys into a spherical basket. In various embodiments, different spherical radii are contemplated. In various embodiments, geometries other than spheres are contemplated, including geometries based on desired treatment margin. In an embodiment, the wires of the basket define multiple openings, which are sufficiently sized to receive the tip portion of microwave ablation device 24. Similar to plug 500, in an embodiment, plug 600 may be covered with a textile material is doped with a substance to be delivered to tissue or the plug 600 may be lined or coated with the substance or a doped sleeve may be disposed around the plug 600.

Figure 7A:
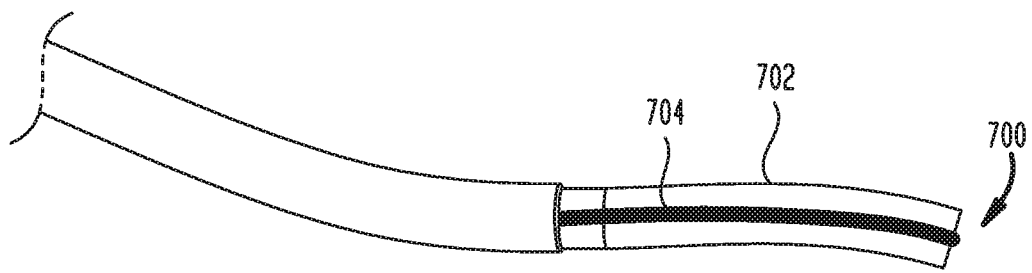
FIGS. 7A-7C are various views of an implant for use with the microwave ablation system for treating tissue, according to yet another embodiment of the present disclosure.
Figure 7B:
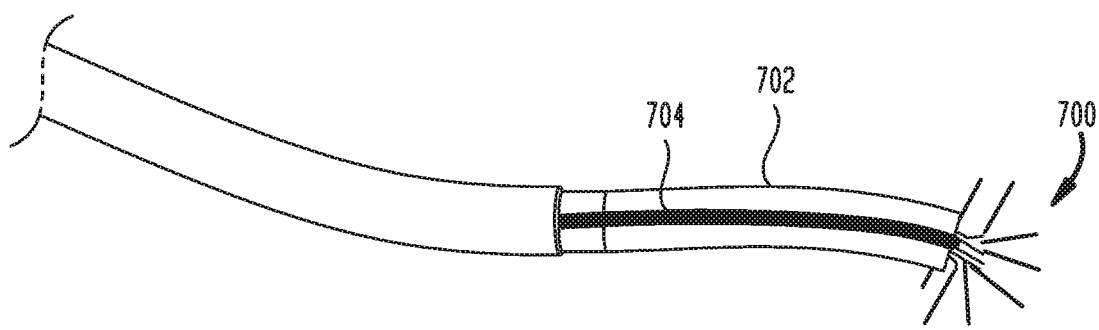
Figure 7C:
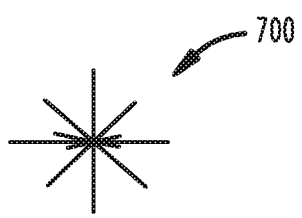

In another embodiment, as illustrated in FIGS. 7A-7C, a plurality of tines 700 is employed as the implant. In this regard, the tines 500 may have any one of numerous configurations. For example, the tines 700 may be made of a shape memory alloy, each tine being permanently strained so as to transform from one shape to another shape, in response to thermal inducement or mechanical inducement via release of a load. In an embodiment, the tines 700 each may be permanently strained to form L- or V-shaped wires, where the angles of two or more of the L- or V-shaped wires vary. To provide further variety among the tines 700, two or more of the L- or V-shaped wires may have different lengths. As a result, when the tines 700 are deployed in the expanded state, they form bristles that extend outward to have a ball-shape appearance. When in the contracted state, the tines 700 may also have any one of numerous configurations. For example, the configurations include, but are not limited to one or more of the tines 700 being folded over itself, one or more of the tines 700 extending substantially in the same direction, one or more of the tines 700 may be rolled up, or another configuration suitable for retaining the tines 700 in a contracted state while being temporarily coupled to a wire 704 within the tube 702 of the implant delivery tool 16.

Returning now to FIG. 1, the microwave ablation system 10 includes a computing device 100 storing one or more ablation planning and electromagnetic tracking applications, a touch display computer 110, microwave ablation generator 115, an operating table 120, including an electromagnetic (EM) field generator 121, a second display 130, an ultrasound imaging sensor 140, an ultrasound workstation 150, a microwave ablation antenna assembly 160, and a base unit 170 configured to support computing device 100, the microwave ablation generator 115, and the touch display computer 110. Computing devices described herein may be, for example, a laptop computer, desktop computer, tablet computer, or other similar device. Touch display computer 110 is configured to control microwave generator 115, pump 117 (FIG. 8), microwave ablation antenna assembly 160, and other accessories and peripheral devices relating to, or forming part of, microwave ablation system 10. Touch display computer 110 is configured to present a user interface enabling a clinician to input instructions and settings for the microwave ablation generator 115, display images, and/or messages relating to the performance of the microwave ablation generator 115, the progress of a procedure, and issue alarms or alerts related to the same.

Operating table 120 may be any table suitable for use during a surgical procedure, which in certain embodiments includes or is associated with an EM field generator 121. EM field generator 121 is used to generate an EM field during the microwave ablation procedure and forms part of an EM tracking system, which is used to track the positions of surgical instruments, e.g., microwave ablation antenna assembly 160 and ultrasound sensor 140, within the EM field around and within the body of a patient. Second display 130, in association with computing device 100, may be used for displaying ultrasound imaging and providing visualization of tissue to be treated as well as navigation of the microwave ablation antenna assembly 160. However, it is envisioned that touch display computer 110 and computing device 100 may also be used for ultrasound imaging and navigation purposes in addition to its microwave ablation generator 115 control functions discussed above.

Electromagnetic energy is generally classified by increasing energy or decreasing wavelength into radio waves, microwaves, infrared, visible light, ultraviolet, X-rays and gamma-rays. As it is used in this description, "microwave" generally refers to electromagnetic waves in the frequency range of 300 megahertz (MHz) ($3\times10^8$ cycles/second) to 300 gigahertz (GHz) ($3\times10^{11}$ cycles/second). As it is used in this description, "ablation procedure" generally refers to any ablation procedure, such as, for example, microwave ablation, radiofrequency (RF) ablation, or microwave or RF ablation-assisted resection.

As will be described in more detail below (FIG. 8) microwave ablation antenna assembly 160 is used to ablate tissue, e.g., a target site, by using microwave energy to heat tissue in order to denature or kill cancerous cells. Further, although an exemplary microwave ablation antenna assembly 160 is detailed herein, it is contemplated that other suitable microwave ablation antennas may be utilized in accordance with the present disclosure. For example, the ablation antennas and systems described in U.S. patent application Ser. No. 14/828,682 entitled MICROWAVE ABLATION SYSTEM, filed on Aug. 18, 2015 by Dickhans, International Application No. PCT/US15/46729 entitled MICROWAVE ABLATION SYSTEM, filed on Aug. 25, 2015 by Dickhans, U.S. patent application Ser. No. 13/836,203 entitled MICROWAVE ABLATION CATHETER AND METHOD OF UTILIZING THE SAME, filed on Mar. 15, 2013 by Ladtkow et al., U.S. patent application Ser. No. 13/834,581 entitled MICROWAVE ENERGY-DELIVERY DEVICE AND SYSTEM, filed on Mar. 15, 2013 by Brannan et al., the entire contents of each of which are incorporated herein by reference, may be used in conjunction with the aspects and features of the present disclosure.

In addition to the EM tracking system, the surgical instruments, e.g., microwave ablation antenna assembly 160, may also be visualized by using ultrasound imaging work station 150. Ultrasound sensor 140, which may be, e.g., an ultrasound wand, may be used to image the patient's body during the microwave ablation procedure to visualize the location of microwave ablation antenna assembly 160 inside the patient's body. Ultrasound sensor 140 may have an EM tracking sensor embedded within or attached to the ultrasound wand, for example, a clip-on sensor or a sticker sensor. Ultrasound sensor 140 may be positioned in relation to microwave ablation antenna assembly 160 such that microwave ablation antenna assembly 160 is at an angle to the ultrasound image plane, thereby enabling the clinician to visualize the spatial relationship of microwave ablation antenna assembly 160 with the ultrasound image plane and with objects being imaged. Further, the EM tracking system may also track the location of ultrasound sensor 140. This spatial depiction of the ultrasound sensor 140 and the microwave ablation antenna assembly 160 is described in greater detail in U.S. Patent Application No. 62/154,924 entitled METHODS FOR MICROWAVE ABLATION PLANNING AND PROCEDURE, filed on Apr. 30, 2015 by Girotto, which is incorporated herein by reference. During surgery, one or more ultrasound sensors 140 may be placed on or inside the body of the patient. EM tracking system may then track the location of such ultrasound sensors 140 and microwave ablation antenna assembly 160 as they are moved relative to each other. It is also envisioned that ultrasound workstation 150 and its related components may be interchanged with real time fluoroscopy, MRI or CT imaging stations.

Figure 8:
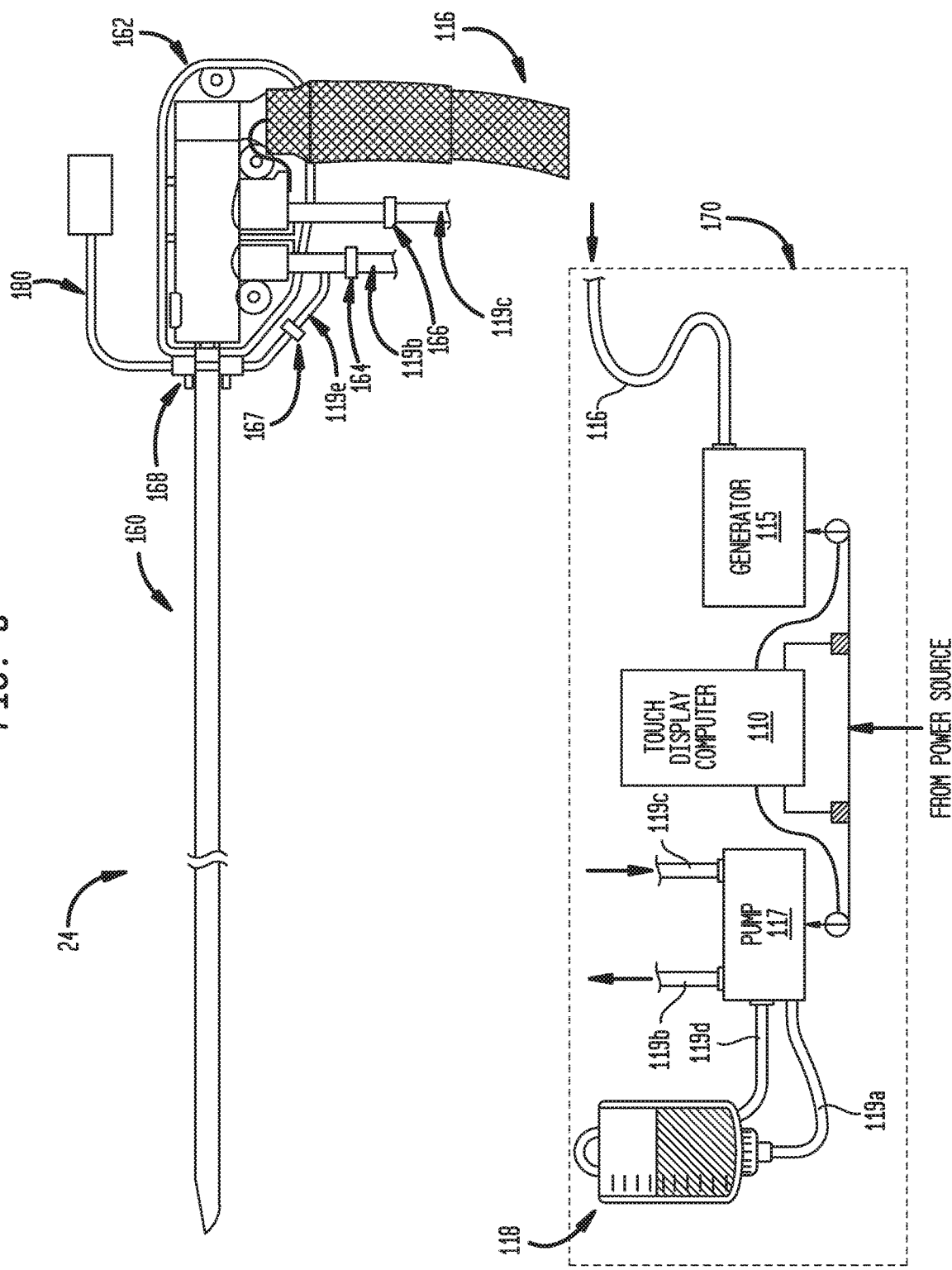
FIG. 8 is a cross-section view of a microwave ablation device and a portion of the microwave ablation system, in accordance with an embodiment of the present disclosure.

With additional reference to FIG. 8, microwave ablation antenna assembly 160, microwave ablation generator 115, touch display computer 110, and a pump 117 are depicted schematically as housed on base unit 170 of system 10 (FIG. 1). Microwave ablation antenna assembly 160 is coupled to a microwave generator 115 via a flexible coaxial cable 116. Microwave generator 115 is configured to provide microwave energy at an operational frequency from about 915 MHz to about 2.45 GHz, although other suitable frequencies are also contemplated. Microwave ablation antenna assembly 160 may include a connection hub 162 for connection of coaxial cable 116, as well as the connection of a fluid inlet port 164 and a fluid outlet port 166. Fluid inlet port 164 permits the ingress of fluid into the microwave ablation antenna assembly 160 for cooling of components housed therein and control of the energy dissipation of microwave energy. Fluid outlet port 166 permits the egress of the fluid following circulation of the fluid through the microwave ablation antenna assembly 160.

The ports 164 and 166 are also coupled to a pump 117 that is, in turn, coupled to a supply source 118 via connection lines 119a, 119d. The supply source 118 may be a fluid filled bag, as depicted in FIG. 6, or any other type of storage unit for any type of fluid such as a tank, reservoir or other container. Pump 117 may be a positive displacement pump, such as a peristaltic pump. The supply source 118 stores a fluid and may maintain the fluid at a predetermined temperature.

Figure 9:
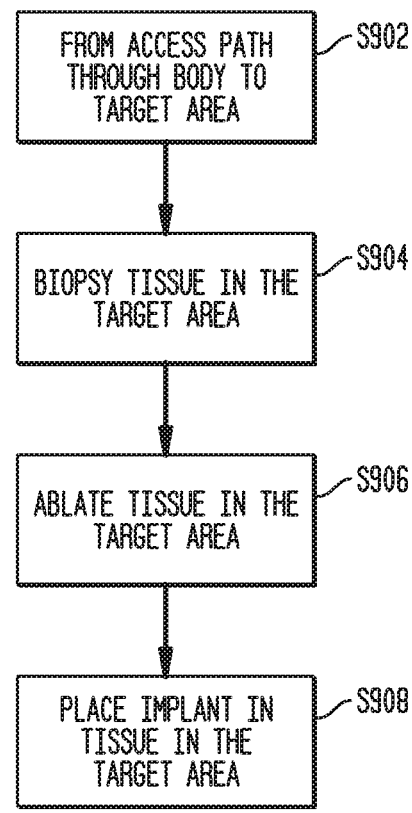
FIG. 9 is a flow diagram of a method of treating tissue, according to an embodiment of the present disclosure.
Figure 10:
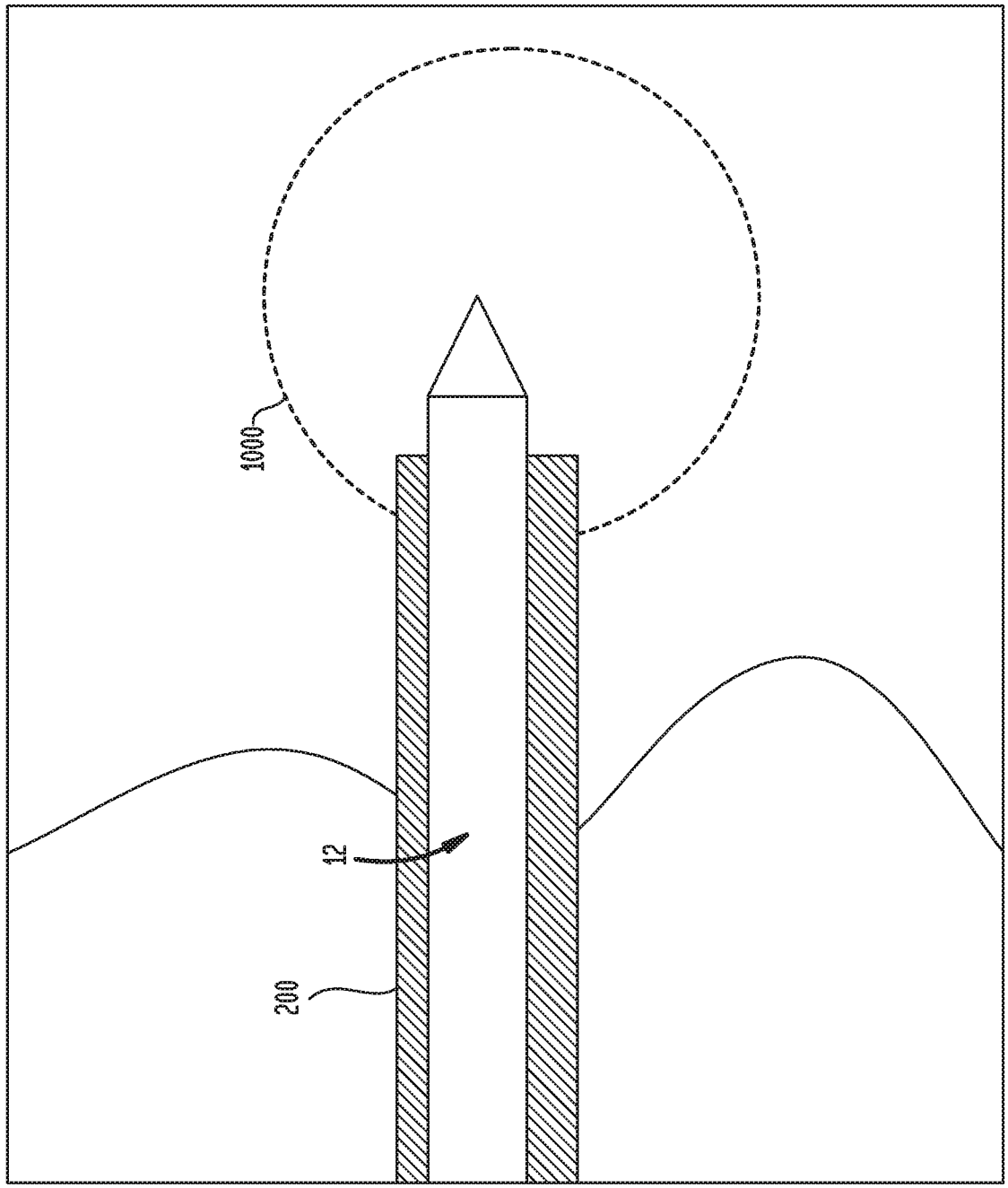
FIGS. 10-16 are simplified schematic diagrams depicting steps of a method of treating tissue, according to an embodiment of the present disclosure.

As noted briefly above, the tools may be used during ablative treatment of a target area within a kidney, liver or other solid tissue, in several different ways. In an embodiment, the tools are used for the purpose of delivering anti-carcinogenic drugs or radiation to the target area. For example, as illustrated in FIG. 9, an access path is formed through the patient's body to a target area of tissue at step S902. In this regard, in an embodiment in which the access tool is formed as part of or is coupled to an access catheter to form an assembly (illustrated in FIG. 10), the access catheter/tool assembly is first inserted into a patient's airway or percutaneously and advanced to an area adjacent to the target area of the tissue. The access catheter/tool assembly provides an access path to the area adjacent to the target area 1000 and is then advanced to puncture the adjacent tissue and thereby form the access path to the target area 1000. Here, the access catheter/tool assembly remains in place. In an embodiment in which the access tool 12 is separate from the access catheter 200, the access catheter 200 initially may be advanced to an area adjacent to the target area 1000 of the tissue, and the access tool 12 may be advanced through the access catheter 200 to puncture the adjacent tissue and provide access to the target area 1000 of the tissue. The access tool 12 may be inserted into the access catheter 200 prior to the access catheter 200 advancing through the patient body or after the access catheter 200 has already been placed in a desired position within the patient's body. In an embodiment, the access tool 12 may be removed. In another embodiment, as will be described in further detail below, the access tool forms an assembly with another tool and thus, remains within the target area of the tissue.

Figure 11:
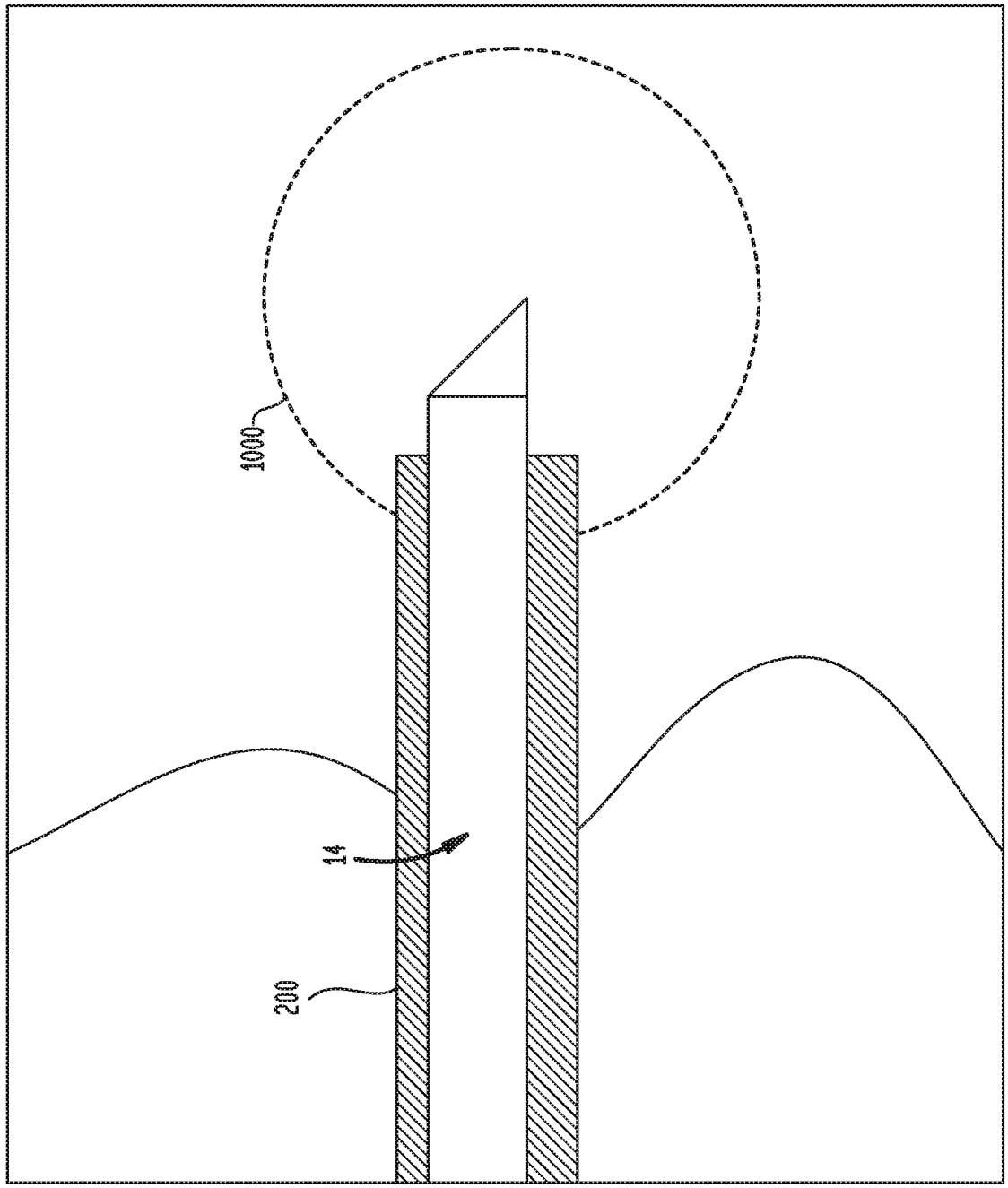

Optionally, a biopsy is taken of the tissue in the targeted area at step S904. The biopsy may be used to establish a baseline for the tissue prior to treatment. In an embodiment as illustrated in FIG. 11, the biopsy tool 14 is advanced through the access catheter 200 to obtain the tissue sample. In another embodiment, the biopsy tool 14 forms an assembly with the access tool 12, and the biopsy tool 14 of the assembly is manipulated to obtain the tissue sample from the targeted area. In any case, after the biopsy is taken, the biopsy tool 14 or the assembly is removed so that a clear path is provided through the access catheter 200.

Figure 12:
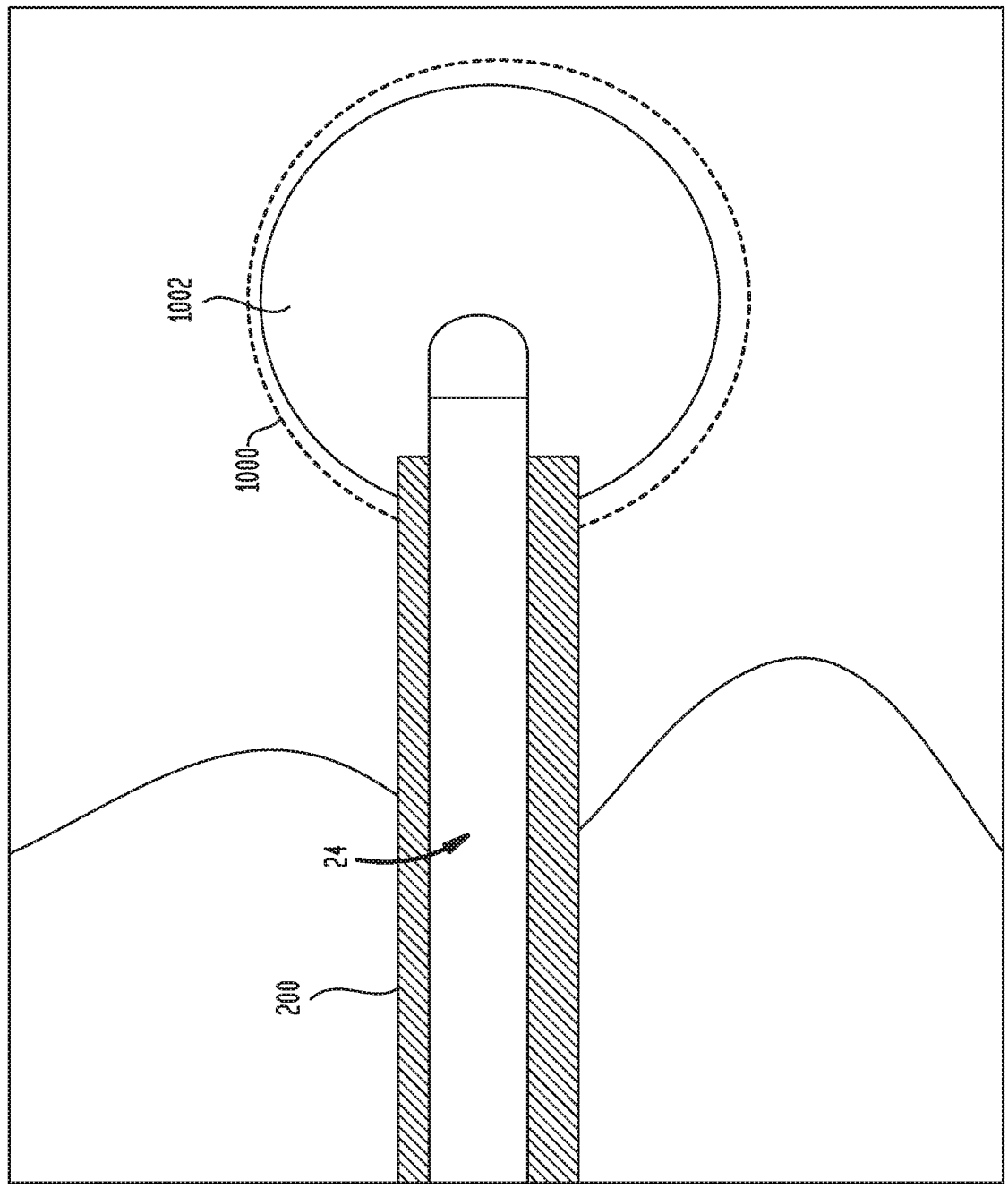

Next, the tissue in the targeted area is ablated at step S906. In addition to using ablation to treat the affected tissue, as depicted in FIG. 12, ablation may also create a pocket 1002 into which the implant 100 may be placed in subsequent steps. The microwave ablation antenna assembly 160 is advanced through the access catheter to the target area of the tissue, and the microwave generator 115 and pump 117 are powered on. Once powered, the microwave generator 115 generates microwave energy which is output from the ablation antenna assembly 160 to heat the tissue to a temperature sufficient to destroy the cells and thereby ablate the tissue. To control the temperature of the heat output from the microwave ablation antenna assembly 160, the pump 117 pumps fluid from the supply source 118 through the antenna assembly 160. In another embodiment, the access tool may incorporate an ablation tool to form an assembly and the ablation tool of the assembly is manipulated to ablate the tissue in the target area. In any case, the ablation tool is then removed.

Figure 13:
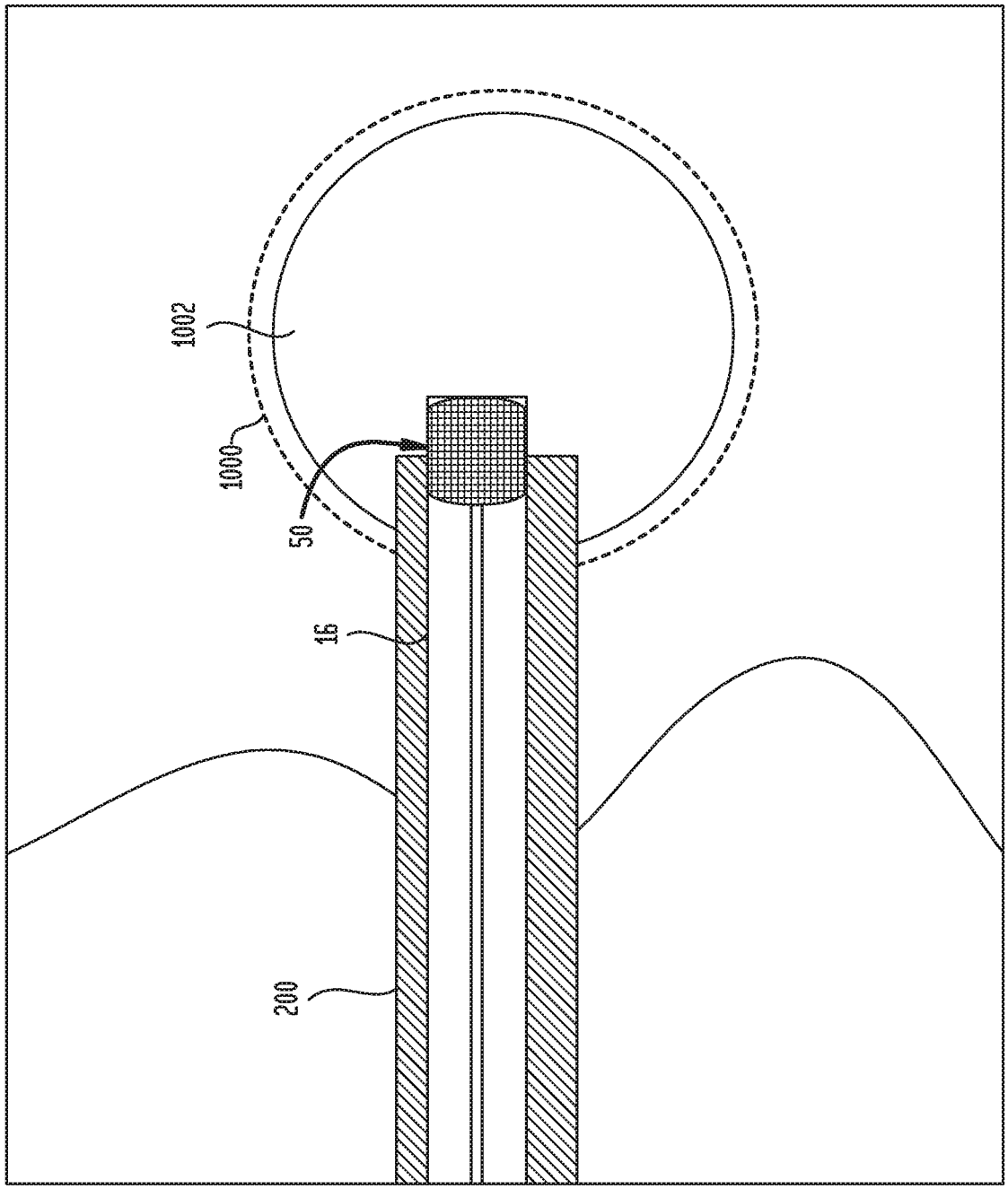
Figure 14:
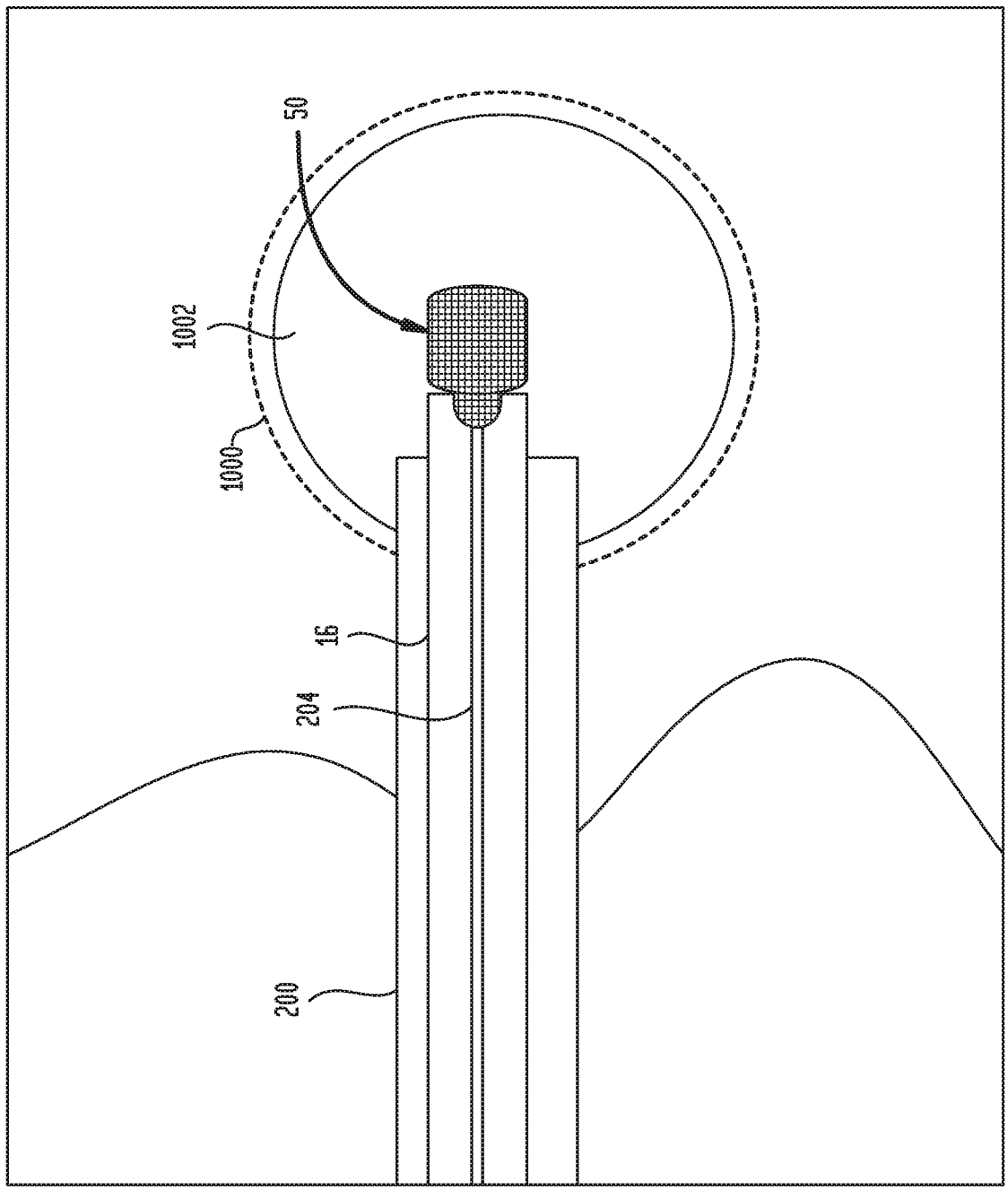
Figure 15:
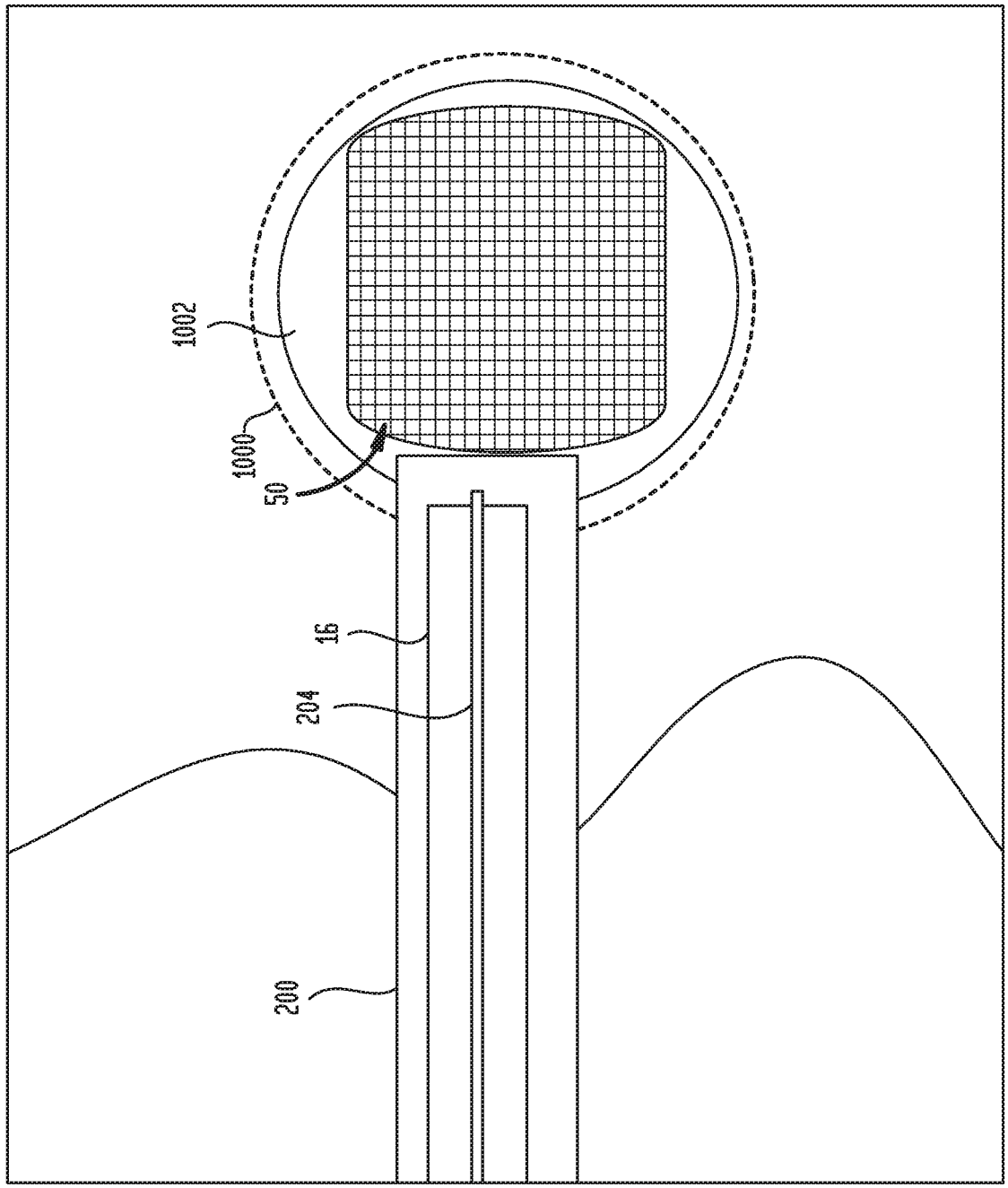

An implant is placed in the tissue in the targeted area at step S708. According to an embodiment as depicted in FIG. 13, implant 50 is delivered using implant delivery tool 16, which is advanced through the access tool or access catheter 200 to the target area 1000 of the tissue. The implant, which is in a contracted state and may be impregnated or doped with a drug, biologic, marker, or other substance, is deployed. Deployment may be achieved by advancing the implant 50 out of a distal opening of the delivery tool 16. For example, as depicted in FIGS. 14 and 15, in a configuration in which the implant 50 is an expandable cage (see also FIGS. 6A-6B), the implant delivery tool 16 is advanced out of the distal opening of the access catheter 200 and the implant 50 is positioned in the tissue at the targeted area 1000. After the implant 50 is suitably positioned, an electrical current, heat or a trigger applied by the wire 204 of the delivery tool 16 to the implant 50 causes the implant to expand. In another embodiment (such as in the embodiment depicted in FIGS. 5A-5C), the implant delivery tool 16 is advanced out of the distal opening of the access catheter 200 so that the implant 500 is placed in the tissue at the targeted area 1000, and then a wire 504 attached to a distal portion of the implant 500 is pulled in a proximal direction causing the implant 500 to shorten lengthwise and expand radially. In still another embodiment in which the implant 50 is in a deformed state when contracted (for example, including folded or varying length tines 700 as depicted in FIGS. 7A-7B), the implant delivery tool 16 is advanced out of the distal opening of the access catheter 200 to place the implant 700 into position in the tissue at the targeted area 1000. According to an embodiment, as each tine 700 exits the access catheter 200, the tine resumes its original, permanent shape. In another embodiment, a temperature change or a mechanical trigger is applied to the implant 700 via or through the wire 704 of the implant delivery tool 16 to cause each tine 700 to resume its original, permanent shape.

Once the implant 50 (or implant 500, 600, 700) is suitably positioned and configured, the implant delivery tool 16 releases the implant 50 and is retracted from the access catheter 200 for removal. In any case, the implant delivery tool 16 is then removed, while the implant 50 remains in the tissue. By using the implant 50 as a substance delivery device, among other things, tissue that may not have been ablated may continue to receive treatment to thereby expand an ablative margin of the targeted area of the tissue. Moreover, loco-regional disease suppression may result. In addition, the risks of hemotoxic effects may be minimized as a result of avoiding the use of the patient's circulatory system as a substance delivery vehicle.

Figure 17:
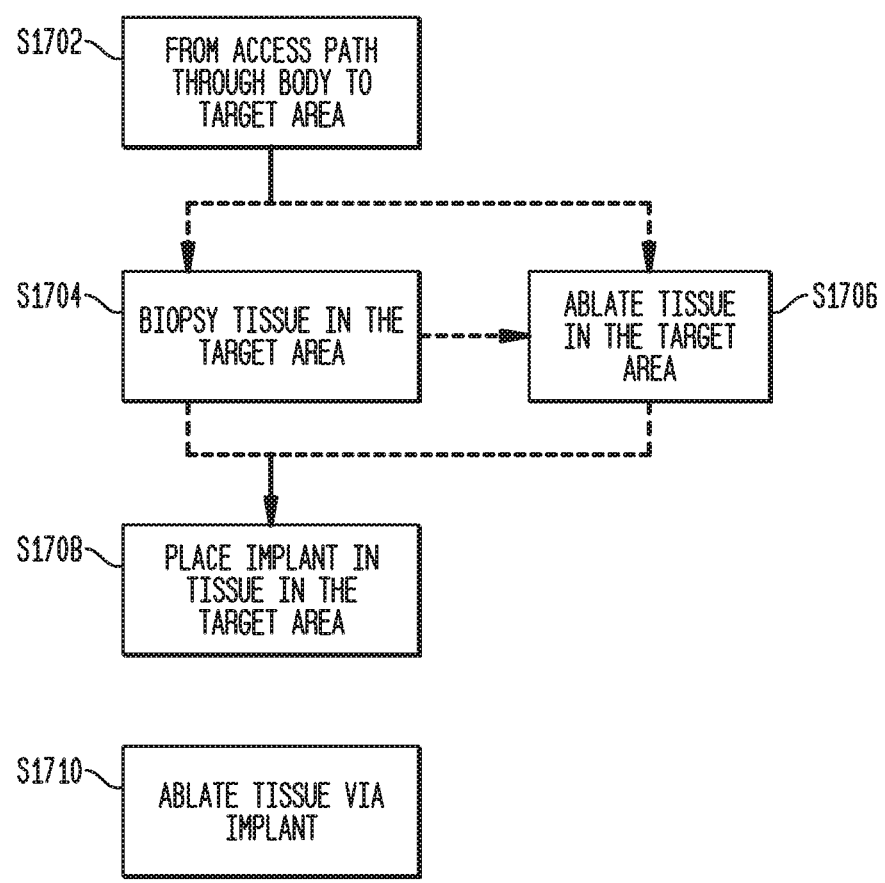
FIG. 17 is a flow diagram of a method of treating tissue, according to another embodiment of the present disclosure.

In accordance with another embodiment of a method of using the tools for treating tissues, in addition to or as an alternative to serving as a substance delivery device, the implant is employed to shape the boundary of the ablative energy emitted from the microwave ablation device. With reference to FIG. 17, an access path is formed through the patient's body to a target area of tissue at step S1702 in a manner similar to that described in relation to steps S902 of method 900 and depicted in FIG. 10. Optionally, a biopsy is taken of the tissue in the targeted area at step S1704 in a manner similar to that described in step 904 in relation to method 900 and depicted in FIG. 11. In another optional embodiment, the tissue in the targeted area is ablated at step S1706 in a manner similar to that described in step S906 in method 900 and depicted in FIG. 12. In any case, the access tool or biopsy tool are removed to provide a clear path through the access catheter.

Figure 16:
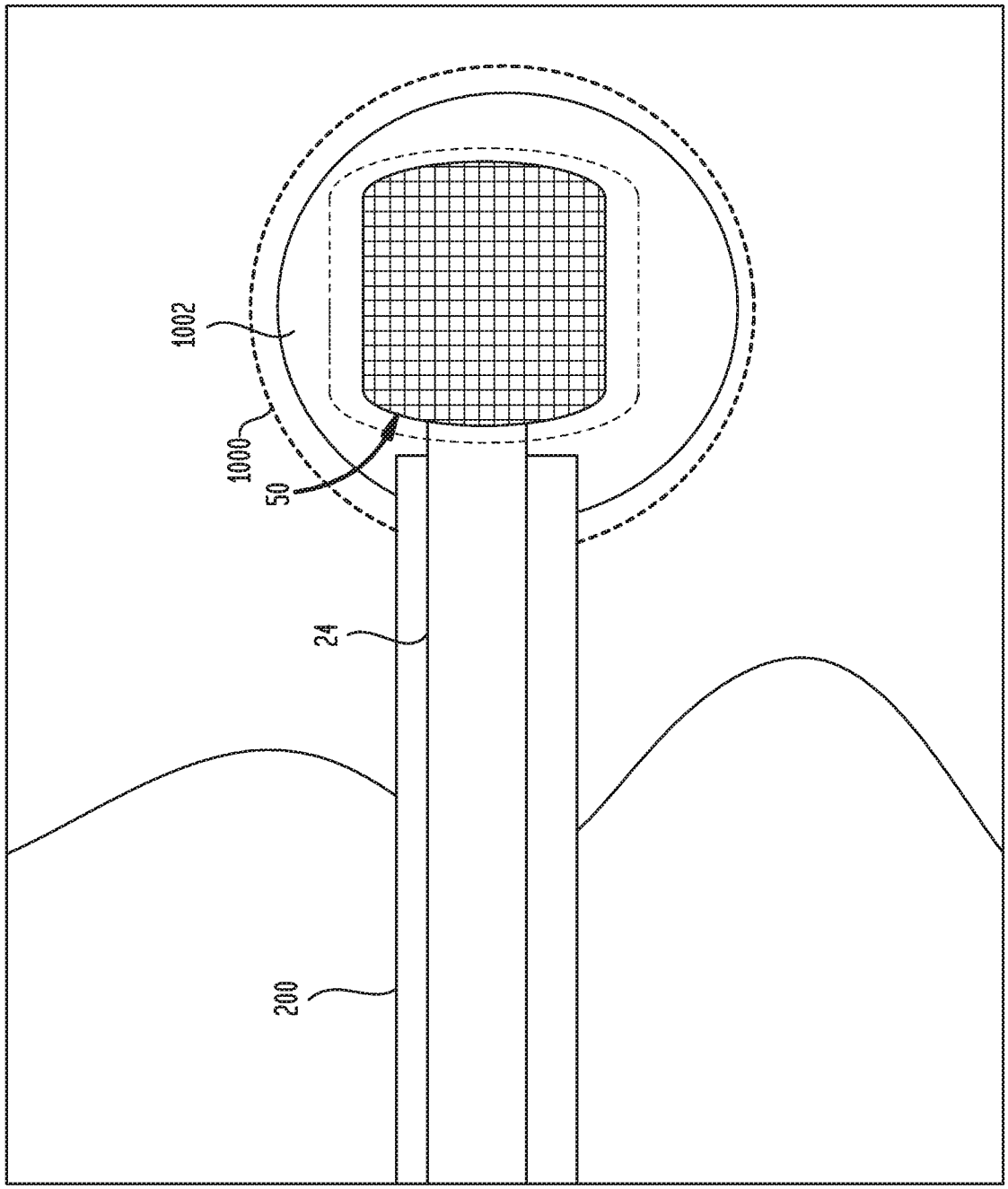

Next, an implant is placed in the tissue in the targeted area at step S1708. For example, an implant having a particular expanded state size and shape is selected and depending on its particular configuration, the implant is deployed in a manner similar to those described above with respect to step S908 and depicted in FIGS. 14 and 15. Specifically, by selecting an implant 50 having a particular expanded state size and shape, the ablative energy output by the microwave ablation device may be shaped, for example, as a sphere, a cylinder or another desired shape. In various embodiments, the implant 50 may include linearly extended elements, such as radially biased tines that are independent from each other, which deploy into a pre-biased radius and wraps back onto the deployment origin. Additionally, the selected implant size and shape may be selected to mark the ablative zone longitudinally. In particular, the length of the tissue to be treated may be marked by selecting an implant 50 having a corresponding length. After the implant 50 is suitably positioned within the tissue at the targeted area 1000, the ablation device 24 is inserted into the implant to thereby ablate tissue at step S1710 and as depicted in FIG. 16. Specifically, by selecting the implant size and shape, an ablation zone formed by ablative energy emitted from a tip of a microwave ablation device 24 may be controlled by the implant 50. Further, in configurations in which the implant 50 is intended to remain within the tissue, the microwave radiation from the microwave ablation device 24 may activate the dopant or substance associated with the implant 50.

Figure 18:
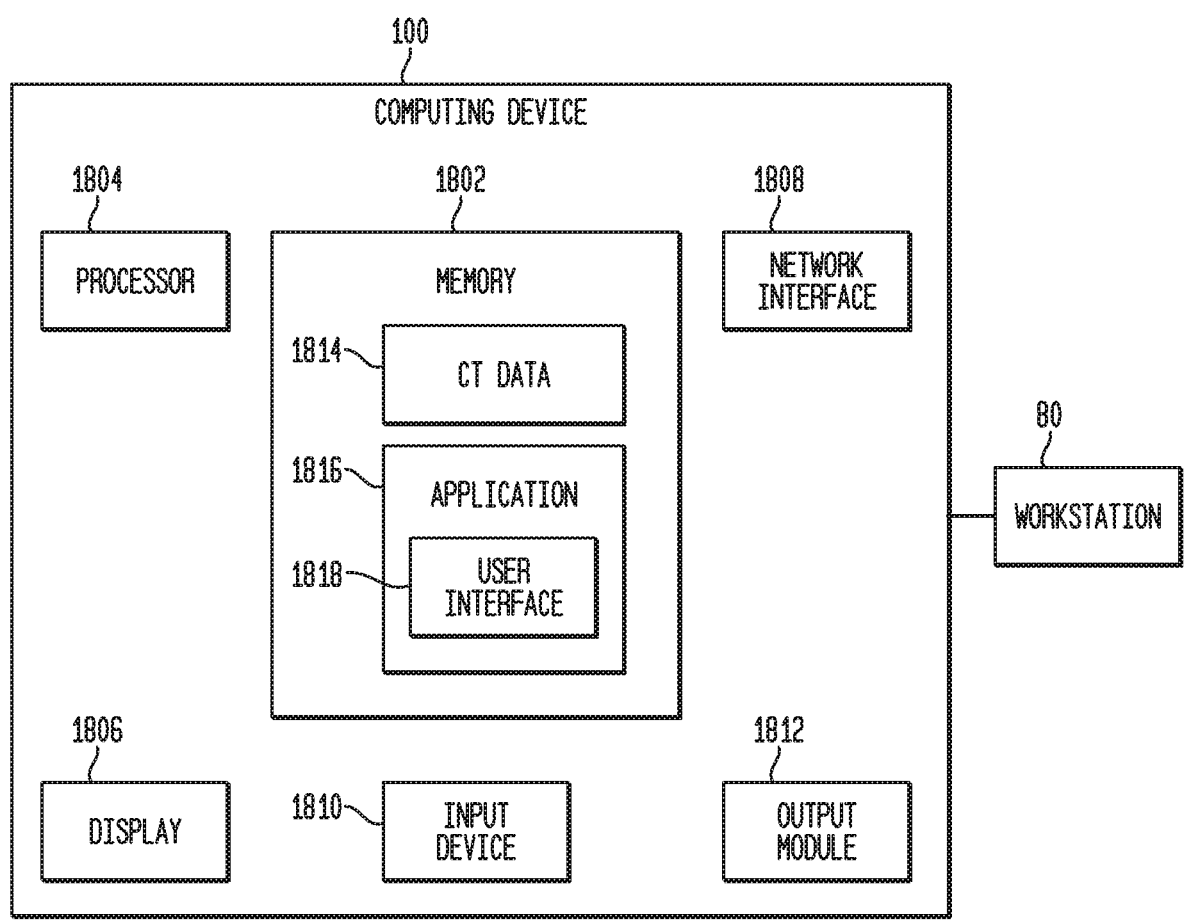
FIG. 18 is a block diagram of a computing device that may be implemented as part of the microwave ablation system, in accordance with an embodiment of the present disclosure.

To operate the microwave ablation system 10, it will be appreciated that the computing device 100 includes a memory 1802, a processor 1804, display 1806, a network interface 1808, an input device 1810, and/or an output module 1812, as illustrated in FIG. 18.

The memory 1802 includes any non-transitory computer-readable storage media for storing data and/or software that is executable by the processor 1804 and which controls the operation of a workstation 80. In an embodiment, the memory 1802 may include one or more solid-state storage devices such as flash memory chips. Alternatively or in addition to the one or more solid-state storage devices, the memory 1802 may include one or more mass storage devices connected to the processor 1804 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 1804. That is, computer readable storage media includes non-transitory, volatile and non-volatile, removable and non-removable media implemented in any method or technology for storage of information such as computer-readable instructions, data structures, program modules or other data. For example, computer-readable storage media includes RAM, ROM, EPROM, EEPROM, flash memory or other solid state memory technology, CD-ROM, DVD, Blu-Ray or other optical storage, magnetic cassettes, magnetic tape, magnetic disk storage or other magnetic storage devices, or any other medium which can be used to store the desired information and which can be accessed by the workstation 80.

The memory 1802 may store an application 1816. The application 1816 may, when executed by the processor 1804, cause the display 1806 to present the user interface 1818. The network interface 1808 may be configured to connect to a network such as a local area network (LAN) consisting of a wired network and/or a wireless network, a wide area network (WAN), a wireless mobile network, a Bluetooth network, and/or the internet. The input device 1810 may be any device by means of which a user may interact with the workstation 80, such as, for example, a mouse, keyboard, foot pedal, touch screen, and/or voice interface. The output module 1812 may include any connectivity port or bus, such as, for example, parallel ports, serial ports, universal serial busses (USB), or any other similar connectivity port known to those skilled in the art.

As it is used in this description, "length" may refer to electrical length or physical length. In general, electrical length is an expression of the length of a transmission medium in terms of the wavelength of a signal propagating within the medium. Electrical length is normally expressed in terms of wavelength, radians or degrees. For example, electrical length may be expressed as a multiple or sub-multiple of the wavelength of an electromagnetic wave or electrical signal propagating within a transmission medium. The wavelength may be expressed in radians or in artificial units of angular measure, such as degrees. The electrical length is in general different from the physical length. By the addition of an appropriate reactive element (capacitive or inductive), the electrical length may be made significantly shorter or longer than the physical length.

Various embodiments of the presently disclosed energy-delivery device with a fluid-cooled probe assembly including a balun are suitable for microwave or RF ablation and for use to pre-coagulate tissue for microwave or RF ablation-assisted surgical resection. Although various methods described hereinbelow are targeted toward microwave ablation and the complete destruction of target tissue, it is to be understood that methods for directing electromagnetic radiation may be used with other therapies in which the target tissue is partially destroyed or damaged, such as, for example, to prevent the conduction of electrical impulses within heart tissue. In addition, the teachings of the present disclosure may apply to a monopole, dipole, helical, or other suitable type of microwave antenna or RF electrode.

This description may use the phrases "in an embodiment," "in embodiments," "in some embodiments," or "in other embodiments," which may each refer to one or more of the same or different embodiments in accordance with the present disclosure.

Although embodiments have been described in detail with reference to the accompanying drawings for the purpose of illustration and description, it is to be understood that the inventive processes and apparatus are not to be construed as limited thereby. It will be apparent to those of ordinary skill in the art that various modifications to the foregoing embodiments may be made without departing from the scope of the disclosure.

What is claimed is:

1. A kit for treating a target area of tissue, the kit comprising:
    an access catheter defining a lumen;
    an access tool configured during use to be advanced longitudinally through the lumen defined by the access catheter such that the access tool extends distally from a distal end of the access catheter to form a path from external to a patient to the target area of tissue within the patient, the access tool including an elongated tube configured to be received within the lumen defined by the access catheter and an elongated shaft configured to be received within a lumen defined by the elongated tube, wherein the elongated shaft has a distal piercing tip and is configured to move within the lumen defined by the elongated tube to move the distal piercing tip relative to a distal end of the elongated tube;
    a biopsy tool for obtaining a tissue sample from the target area of tissue, the biopsy tool configured during use to be inserted through the lumen defined by the access catheter after advancement of the access catheter to the target area of tissue and removal of the access tool from the access catheter;
    an implant deployment tool including a tube configured to be inserted into the lumen defined by the access catheter;
    an implant configured to be deployed within the target area of tissue, the implant disposed within the tube of the implant deployment tool in a contracted state and being slidable out of a distal opening of the tube of the implant deployment tool into the target area of tissue and expandable into an expanded state, wherein the implant includes a plurality of tines, each tine of the plurality of tines being strained into one of an L-shaped wire or a V-shaped wire having at least one free end such that each tine of the plurality of tines forms a bristle extending radially outward to define a ball-shape of the implant when the implant is in the expanded state; and
    a microwave delivery device configured to:
        be advanced through the lumen defined by the access catheter and slidably disposed within the implant when the implant is in the expanded state and deployed within the target area of tissue; and
        deliver microwave energy to the target area of tissue while disposed within the implant when the implant is in the expanded state and deployed within the target area of tissue to form an ablation zone such that the implant surrounds the ablation zone to control a size of the ablation zone.

2. The kit of claim 1, wherein the implant is doped with radioactive material.

3. The kit of claim 1, wherein the implant includes a drug.

4. The kit of claim 1, wherein the implant includes a biologic.

5. The kit of claim 1, wherein one or more of the plurality of tines folds over itself in the contracted state.

6. The kit of claim 1, wherein a first tine of the plurality of tines has an end portion that, upon deployment out of a distal opening of the implant deployment tool, extends radially relative to a longitudinal axis of the implant deployment tool.

7. The kit of claim 6, wherein a second tine of the plurality of tines has an end portion that, upon deployment out of the distal opening of the implant deployment tool, extends radially relative to the longitudinal axis of the implant deployment tool, and an angle of deployment of the first tine is less than an angle of deployment of the second tine.

8. The kit of claim 1, wherein the implant comprises a shape memory alloy forming a wire basket in the expanded state.

9. A kit for treating a target area of tissue, the kit comprising:
    an access catheter defining a lumen;
    an access tool configured during use to be advanced longitudinally through the lumen defined by the access catheter such that the access tool extends distally from a distal end of the access catheter to form a path from external to a patient to the target area of tissue within the patient, the access tool including an elongated tube configured to be received within the lumen defined by the access catheter and an elongated shaft configured to be received within a lumen defined by the elongated tube, wherein the elongated shaft has a distal piercing tip and is configured to move within the lumen defined by the elongated tube to move the distal piercing tip relative to a distal end of the elongated tube;

a biopsy tool for obtaining a tissue sample from the target area of tissue, the biopsy tool configured during use to be inserted through the lumen defined by the access catheter after advancement of the access catheter to the target area of tissue and removal of the access tool from the lumen defined by the access catheter;

an implant deployment tool configured to be inserted into the lumen defined by the access catheter;

an implant disposed within the implant deployment tool in a contracted state, the implant configured to slide out of a distal opening of the implant deployment tool into a target area of tissue and expand into an expanded state, wherein the implant includes a plurality of tines, each tine of the plurality of tines being strained into one of an L-shaped wire or a V-shaped wire having at least one free end such that each tine of the plurality of tines forms a bristle extending radially outward to define a ball-shape of the implant when the implant is in the expanded state; and a microwave energy delivery device configured to deliver microwave energy to the target area of tissue.

10. The kit according to claim 9, wherein the implant is configured to shape a boundary of the microwave energy delivered by the microwave energy delivery device to the target area of tissue.

11. The kit according to claim 1, wherein the microwave delivery device is a microwave antenna.

12. The kit according to claim 9, wherein the microwave energy delivery device is a microwave antenna.

13. The kit according to claim 1, further comprising a wire disposed within the tube and having a distal end portion removably coupled to a distal end portion of the implant, the wire configured to be pulled proximally through the tube of the implant deployment tube to correspondingly pull the distal end portion of the implant toward a proximal end portion of the implant, thereby decreasing a length of the implant and transitioning the implant from the contracted state to the expanded state.

14. The kit according to claim 1, wherein a length of the implant when disposed within the tube and in the contracted state is greater than the length of the implant when deployed into the target area of tissue and in the expanded state.

15. The kit according to claim 1, wherein the biopsy tool includes a distal cutting edge.

16. The kit according to claim 1, wherein the biopsy tool includes a brush portion for obtaining the tissue sample.

17. The kit according to claim 9, wherein the biopsy tool includes a distal cutting edge.

18. The kit according to claim 9, wherein the biopsy tool includes a brush portion for obtaining the tissue sample.

* * * * *